United States Patent [19]
Jackson

[11] Patent Number: 5,941,885
[45] Date of Patent: Aug. 24, 1999

[54] TOOLS FOR USE IN INSTALLING OSTEOSYNTHESIS APPARATUS UTILIZING SET SCREW WITH BREAK-OFF HEAD

[76] Inventor: Roger P. Jackson, 4706 W. 86th St., Prairie Village, Kans. 66207

[21] Appl. No.: 08/726,828

[22] Filed: Oct. 8, 1996

[51] Int. Cl.⁶ .................................................. A61B 17/56
[52] U.S. Cl. .............................................................. 606/104
[58] Field of Search .............................. 606/104, 61, 60, 606/86, 72, 73

[56] References Cited

U.S. PATENT DOCUMENTS

| | | | |
|---|---|---|---|
| 2,248,054 | 7/1941 | Becker | 606/104 |
| 3,604,487 | 9/1971 | Gilbert | 606/104 |
| 3,892,232 | 7/1975 | Neufeld | 606/104 |
| 5,005,562 | 4/1991 | Cotrel . | |
| 5,261,907 | 11/1993 | Vignaud et al. . | |
| 5,312,404 | 5/1994 | Asher et al. . | |
| 5,346,493 | 9/1994 | Stahurski et al. . | |
| 5,352,231 | 10/1994 | Brumfield | 606/104 |
| 5,354,292 | 10/1994 | Braeuer et al. | 606/104 |
| 5,649,931 | 7/1997 | Bryant et al. | 606/104 |
| 5,658,289 | 8/1997 | Boucher et al. | 606/104 |
| 5,662,658 | 9/1997 | Wenstrom, Jr. | 606/104 |

*Primary Examiner*—Guy V. Tucker
*Attorney, Agent, or Firm*—Litman, Kraai & Brown, L.L.C.; John C. McMahon

[57] ABSTRACT

Tools for use in installing osteosynthesis apparatus utilizing a set screw having a break off head, a lower threaded portion and a cylindrical bore extending at least partially through the set screw head. Several of the tools comprise socket type tools having a handle, a stem and a head with a socket formed therein. A projection extends axially into the socket from an inner end of the socket and includes an outwardly biasing element thereon. The projection is sized for insertion into at least a portion of the bore extending into the set screw head, when the set screw head is positioned in the socket. The outwardly biasing element biases against an internal wall of the head which defines the upper section of the cylindrical bore, in order to grip the head. In another tool of the set the tip of the stem is threaded and sized for threaded insertion into the set screw receiving bore of an osteosynthesis implant. Another tool of the set comprises forceps having first and second socket halves formed in opposed grasping portions of the socket. When the grasping portions are advanced together, the first and second socket halves form a socket within which a set screw secured to an implant may be secured to facilitate manipulation of the implant with the set screw secured thereto.

16 Claims, 7 Drawing Sheets

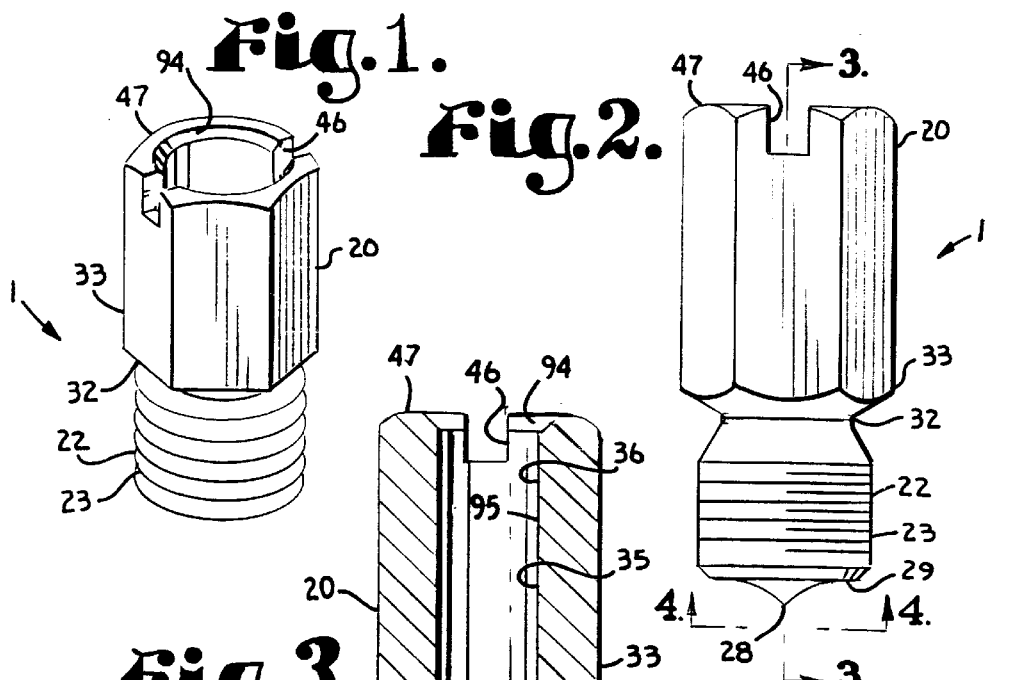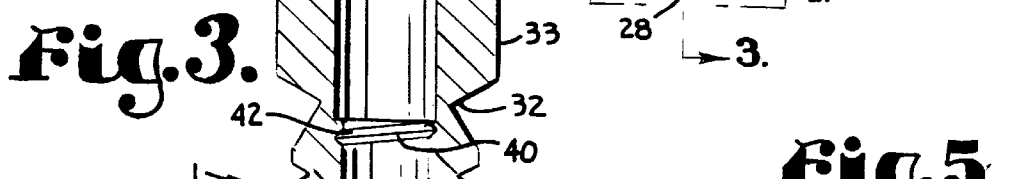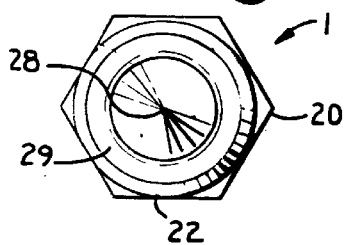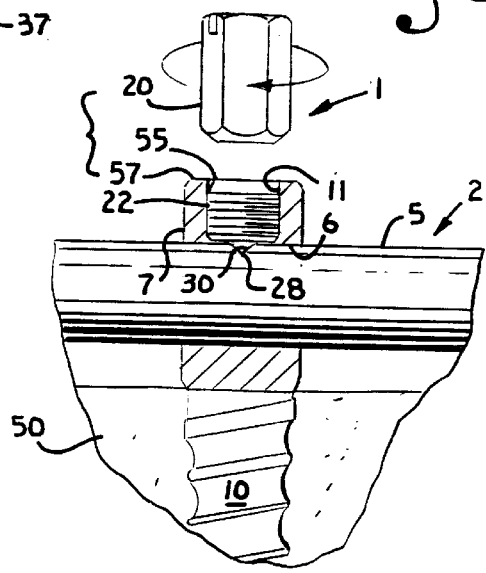

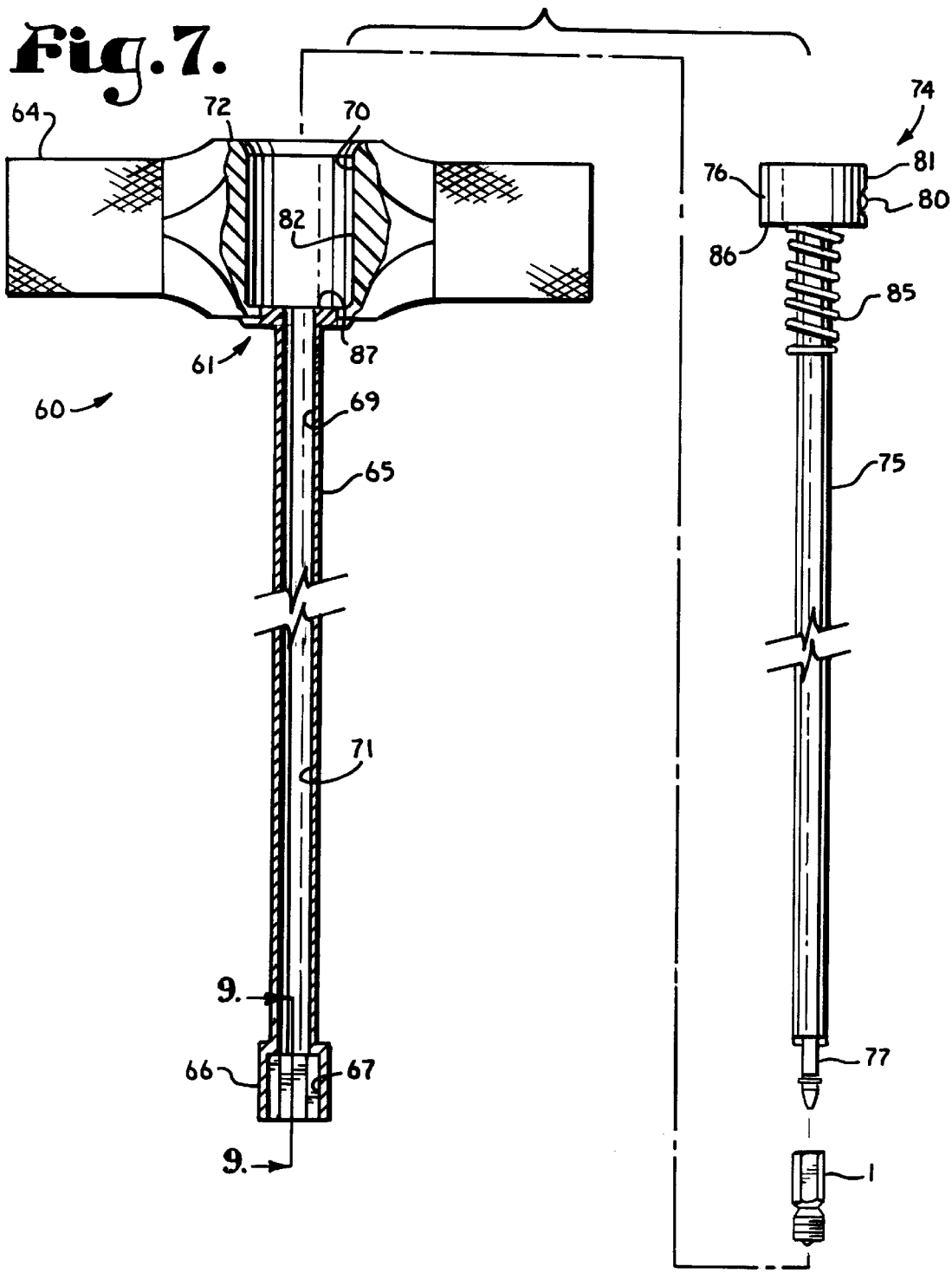

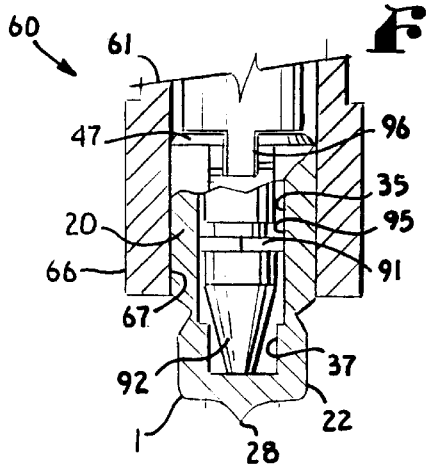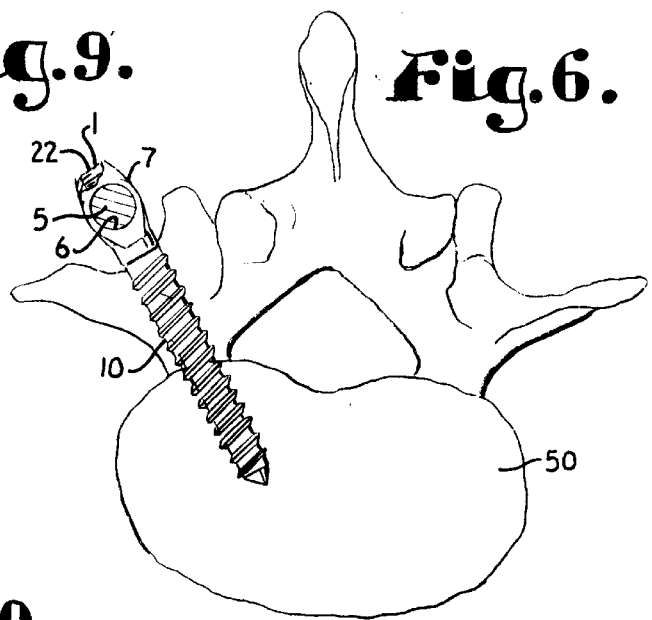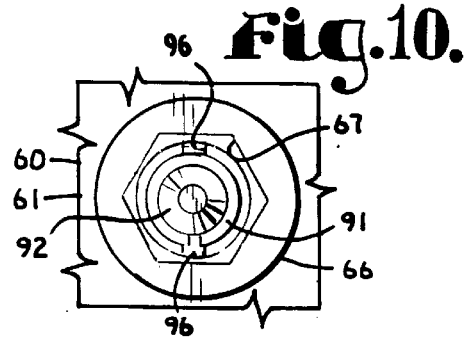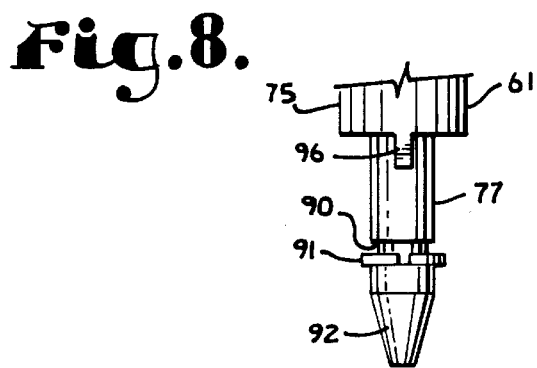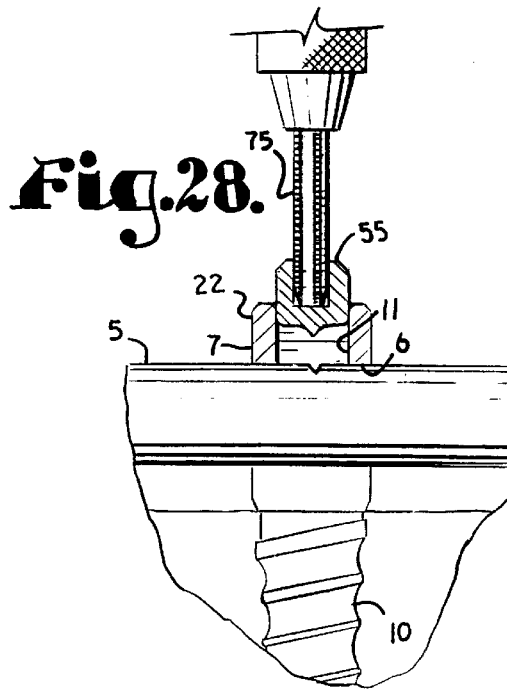

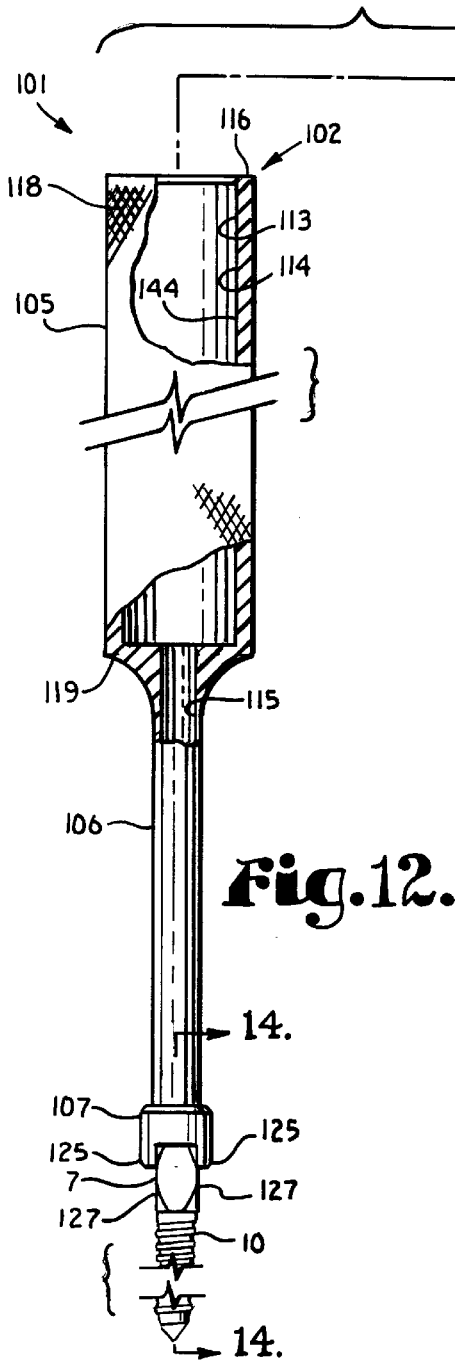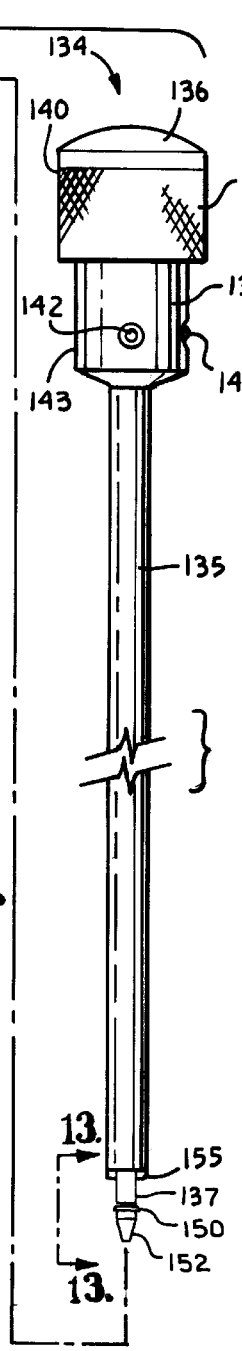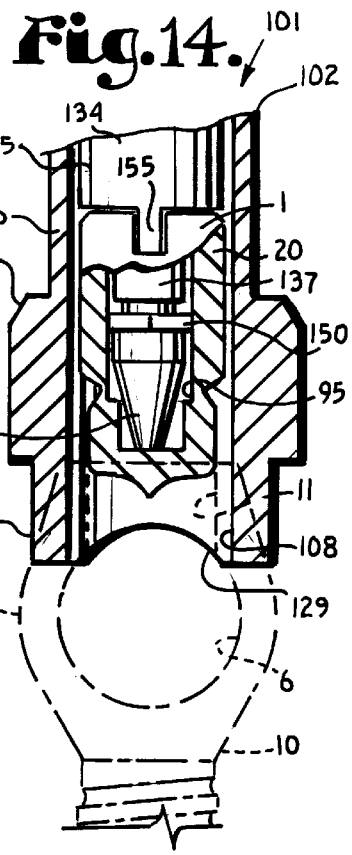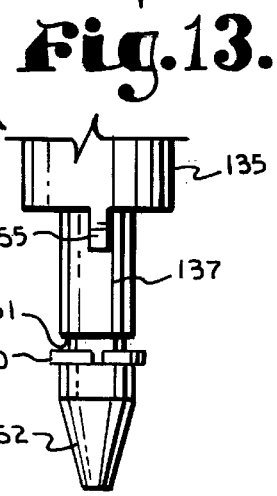
Fig. 14.
Fig. 12.
Fig. 13.

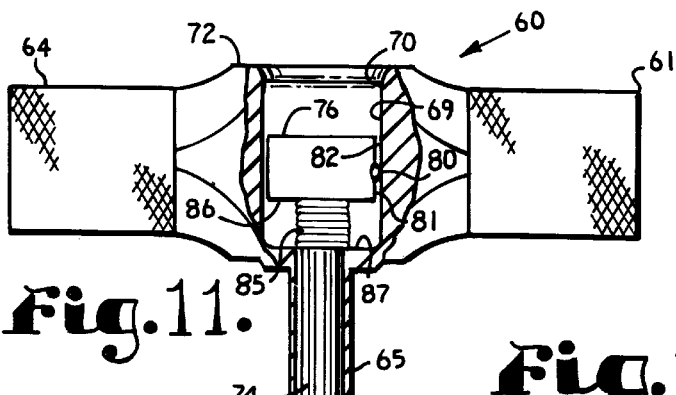
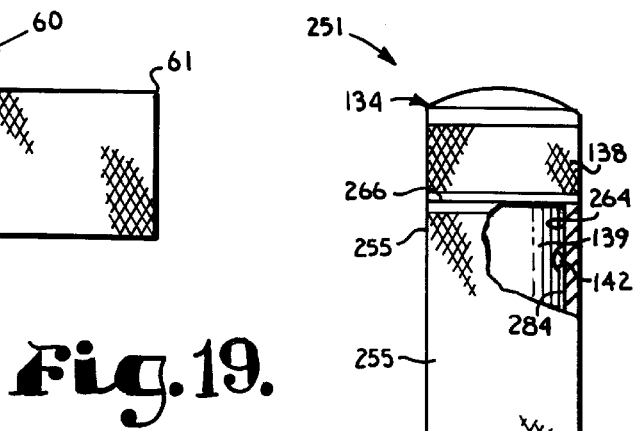
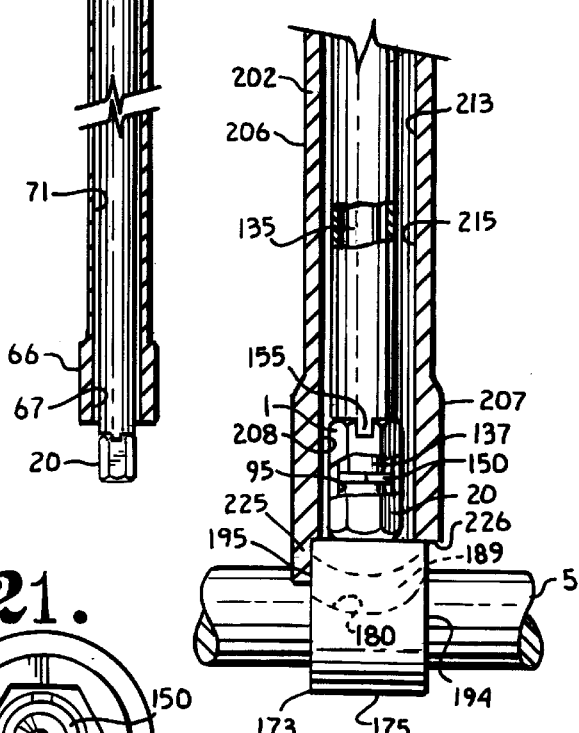
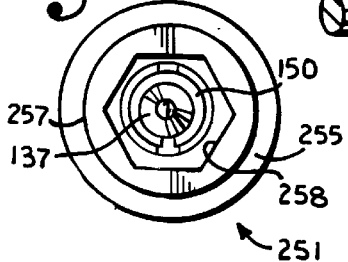

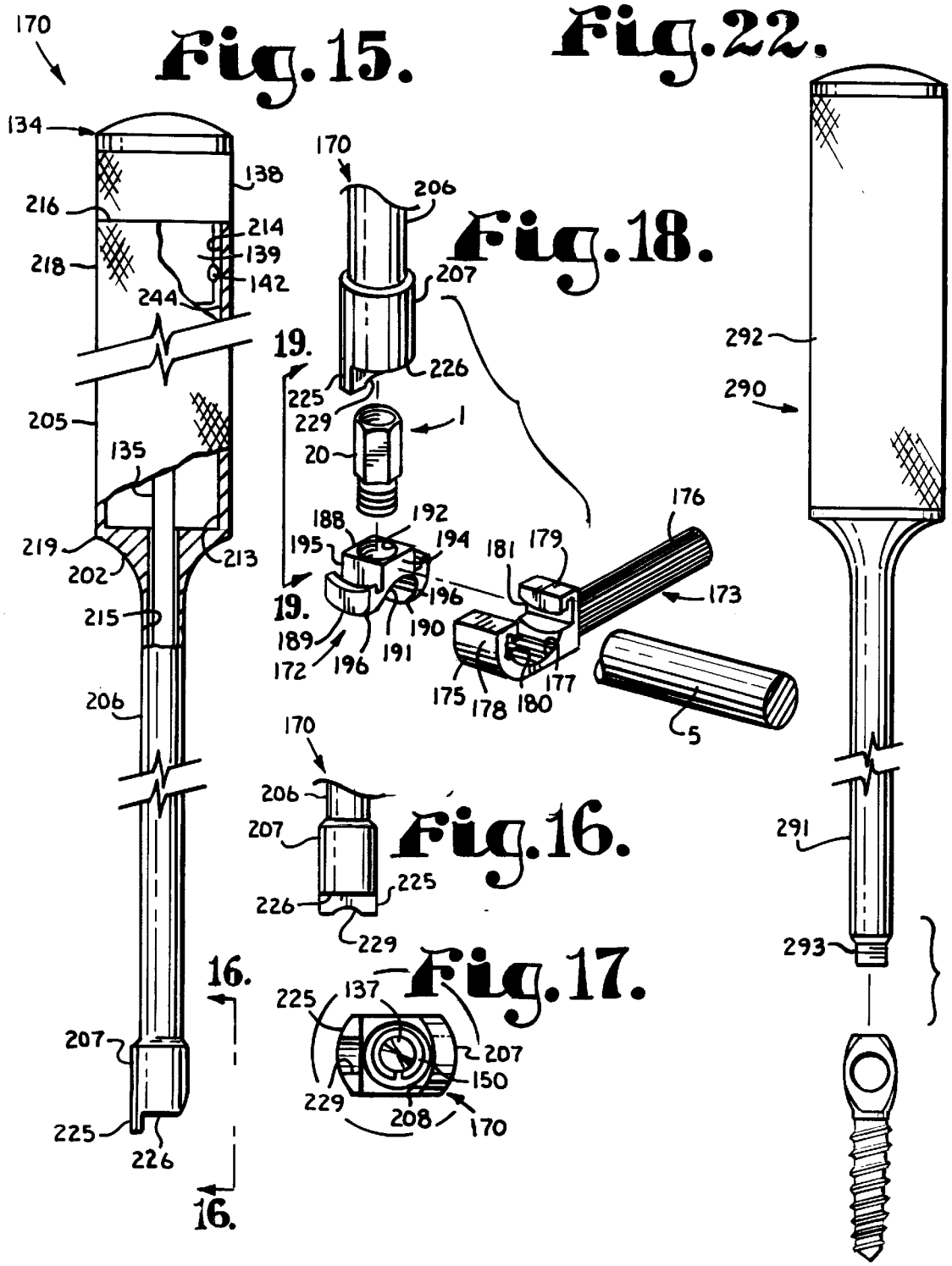

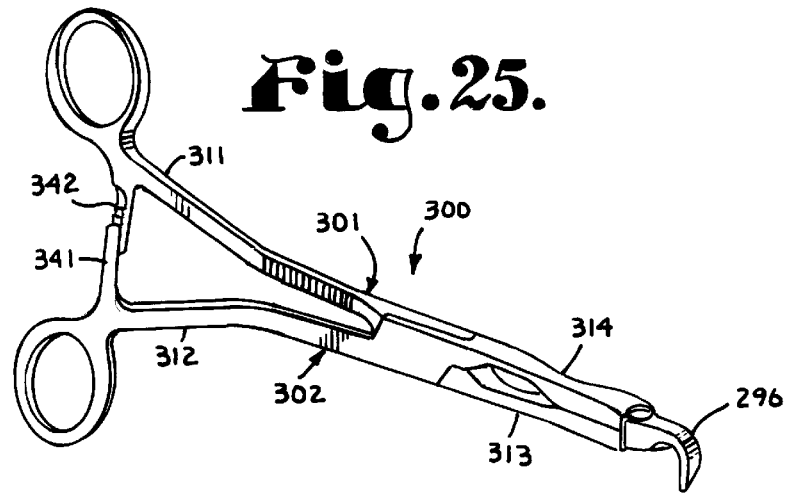
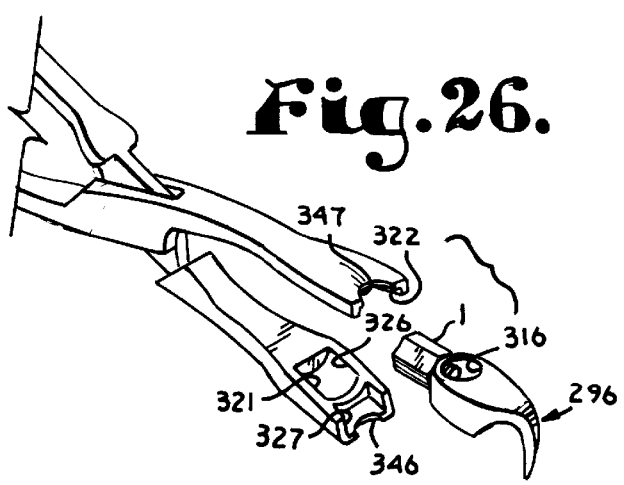
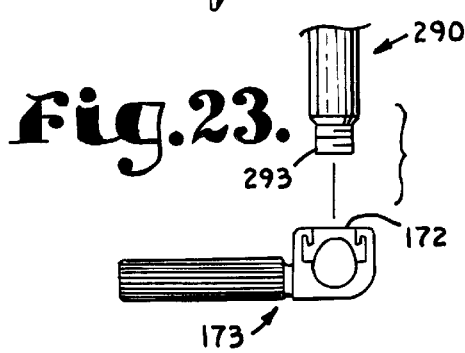
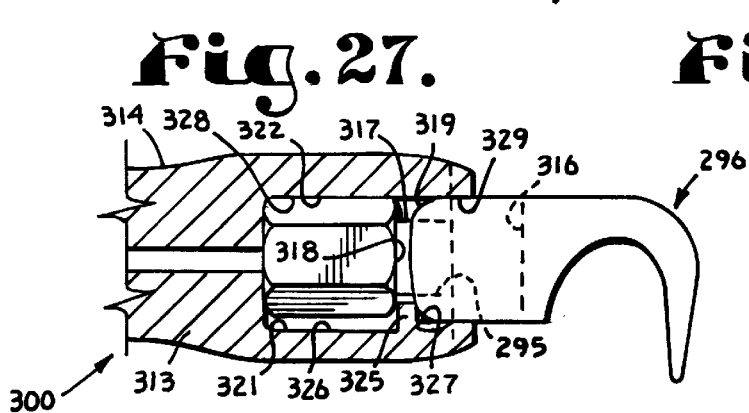
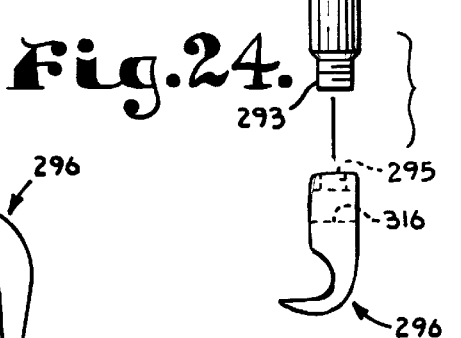

TOOLS FOR USE IN INSTALLING OSTEOSYNTHESIS APPARATUS UTILIZING SET SCREW WITH BREAK-OFF HEAD

BACKGROUND OF THE INVENTION

The present invention relates to tools for use in surgically installing apparatus for correcting orthopedic deformities in a patient and, in particular, to tools specifically designed to facilitate installation of a spinal osteosynthesis system in a patent utilizing a unique set screw having a break-off head.

Spinal osteosynthesis apparatus generally comprise a rod or system of rods which are secured along at least a portion of the spine by bone screws, including sacral screws and pedicle screws, transverse connectors and bone hooks for stabilizing and adjusting spinal alignment. The bone screws, transverse connectors, bone hooks and related items which are intended for use in connecting the rods to the bone and to facilitate adjustment of the rods may collectively be referred to as hardware or implants. In a very basic apparatus, the bone screws have a spinal rod receiving bore extending through a ring or head of the screw. The screws are secured in the vertebra at desired locations and a spinal rod is then extended through the spinal rod bore in each bone screw. Set screws, inserted in threaded bores extending through the wall of the screw ring, preferably perpendicular to the axis of the spinal rod bore, are tightened to fix the translational and rotational relationship of the rods within the bores. The rods may then be bent or formed to support the spine in a desired manner or to exert the desired corrective or stabilizing forces on the spine.

A slightly more complicated system uses transverse connectors in association with the bone screws to secure the spinal rods. The transverse connectors include an arm and a head. The head has a spinal rod bore extending therethrough and the arm is normally equivalent in diameter to the spinal rod. The arm of the connector is inserted through the spinal rod bore in the pedicle screw then the spinal rod may be inserted through the spinal rod bore in the transverse connectors. A threaded bore extends through the head of the connector perpendicular to the axis of the spinal rod bore. Once the rod is inserted through the bore in the transverse connectors the set screws are inserted through the threaded bores and tightened to fix the relative position of the rod within the spinal rod bore and set screws are inserted in the threaded bores and tightened to fix the position of the transverse connector with respect to the pedicle screws.

The pedicle screws, transverse connectors, bone hooks or related implants or hardware may be of the closed end type as discussed above or of an open end type wherein the head of the screw or connector generally incorporates a U-shaped channel or groove, an upper end of which may be closed off by a cap or saddle to form the spinal rod bore. The threaded set screw bore typically extends through the cap. With open end type implants, the spinal rod may be inserted from above, into the U-shaped channel instead of having to insert the spinal rod axially through the rod receiving bores of closed end type implants.

A preferable aspect of any osteosynthesis apparatus is to provide a system wherein the components may be readily manipulated to facilitate relatively easy and rapid installment or disassembly. Manipulation of small headed set screws provides a significant challenge to surgeons installing currently available systems, especially when working in the close confines of an operative site. Some techniques require the surgeon to operate through an opening that is just sufficient in size to receive the parts of the apparatus to be assembled and the tools with no room provided for the surgeon's hands or fingers. Due to the nature of use of the set screw, it is important that the set screw be relatively small to reduce impact on the patient and irritation caused by the screw. The small size of set screws often makes them difficult to grasp and manipulate.

Currently, set screws are being used in which the head of the screw breaks off or shears off after insertion such that generally no or only a small portion of the set screw extends above or beyond the threaded bore into which it is inserted. The broken off head should be readily captured and removed from the site of the operation. There is a need for a set of tools for installing osteosynthesis apparatus incorporating set screws with break off heads in which the tools facilitate manipulation of the set screws and implants utilizing such set screws and removal of the heads after break-off.

SUMMARY OF THE INVENTION

The present invention comprises a set of tools for use in installing an osteosynthesis apparatus utilizing a set screw with a break off head. The set screw comprises a head of polygonal and preferably hexagonal external cross-section, and a lower portion having a threaded outer surface. A peripheral notch is formed between the head and the lower threaded portion of the set screw. A cylindrical axially extending bore is formed in the set screw and extends through the head and partially through the lower portion.

The set screw is adapted for use in securing a rod in the bore of a ring from translational or rotational motion. The ring is of the type formed in the head of a bone screw, the head of a connector secured to the bone screw or the head of a hook. The rod is of the type including spinal rods or the rod portion of a connector. A threaded set screw bore extends radially through a wall of the ring perpendicular to the axis of the rod receiving bore.

The tools of the present invention are generally socket type tools having a handle, a stem and a head with a socket formed therein. A projection extends axially into the socket from an inner surface thereof and has an outwardly biasing element thereon. The projection is sized for insertion into at least a portion of the bore extending through the set screw head, when the set screw head is positioned in the socket. The outwardly biasing element biases against the internal wall of the head defining the upper section of the cylindrical bore, in order to grip the head when inserted therein.

In one tool of the set, a set screw torque wrench, the socket is of hexagonal internal cross-section and is sized to snugly and matingly receive and conform to the hexagonal head of the set screw to facilitate driving of the set screw. After the proper orientation of a rod in a respective ring has been achieved, the set screw driver, having a set screw secured within the socket, can then be used to install a set screw in the threaded set screw bore of the ring, and to tighten down the set screw to engage and bite into the outer surface of the rod. Continued tightening of the set screw to a preselected torque causes the head to shear off along the radially inner circular groove of the peripheral notch so as to break comparatively smoothly along a plane defined by the circular groove. Biasing of the outwardly biasing element against the internal wall of the set screw head holds the head after breaking on the projection to permit retrieval of the head.

A second tool, which is a closed end screw driver, is adapted to drive bone screws of the closed end type with a set screw pre-loaded in a set screw receiving bore thereof. The head of the bone screw driver has depending extensions, ears or tabs adapted to engage opposite sides or faces of the bone screw on an upper end thereof to facilitate driving of the bone screw. When the bone screw driver is positioned over the end of a bone screw with a set screw already secured thereto, the set screw head extends into the driver socket which is cylindrical in cross section and slightly wider than the set screw to permit rotation of the set screw therein. A projection extends into the cylindrical bore in the set screw, as with the set screw driver. The grip on the set screw that is caused by the biasing of the outwardly biasing element against the set screw head internal wall, releasably secures the bone screw to the bone screw driver to facilitate handling and positioning of the bone screw with the bone screw driver.

A third tool, which is a cap inserter, is adapted for inserting caps on bone screws, connectors or bone hooks with a set screw pre-loaded in a set screw receiving bore. The head of the cap inserter includes a single depending projection, ear or tab adapted to abut against a rear face of a cap having a set screw pre-loaded in the set screw receiving bore. To use the cap installer, the head of a set screw that has previously been threaded onto a cap is inserted into the socket of the cap inserter such that the projection extends into the set screw bore and the depending tab abuts against a rear face of the cap.

The cap installer socket is cylindrical and slightly wider than the set screw. The interference fit produced between the outwardly biasing element on the projection and the internal wall of the set screw head releasably secures the set screw and the cap onto the cap installer. Abutment of the depending tab against the rear surface of the cap prevents rotation of the cap relative to the set screw during manipulation of the tool with the cap attached thereto. The tool with the cap attached thereto can then be used to install the cap to the open end of a bone screw, a connector or a bone hook with the set screw already partially threaded therein.

Another tool of the present invention comprises a threaded implant installer comprising a stem having a handle secured at one end and threaded at an opposite end. The threaded end is sized for insertion into and threaded coupling with the threaded set screw bore in a bone screw or other implant such as a hook or connector. The threaded bone screw driver is particularly useful in minimally invasive type surgery wherein the implant is inserted into the body through a relatively small incision. The threaded coupling between the tool and the bone screw prevents the screw from being pulled off the driver, if the screw must be retracted through the incision.

Another tool of the present invention comprises forceps having first and second arms pivotally secured together in a scissor like fashion. Each arm includes a gripping portion and a handle portion. Each gripping portion includes a socket half formed therein such that when the gripping portions of the first and second arms are advanced together the socket halves form a socket which is adapted to receive a portion of an osteosynthesis implant with a set screw secured thereto. One of the socket halves includes a ridge extending thereacross and dividing the socket halve into an inner portion and an outer portion. The inner portion of the socket half is adapted to receive the set screw and the outer portion is adapted to receive the portion of the implant to which the set screw is secured. The ridge extends into a gap between a lower end of the head of the set screw and the end of the implant to which the set screw is attached. The ridge interferingly prevents the set screw and therefore the implant to which it is attached from being removed from the socket when the implant and the set screw are grasped by the grasping portions of the forceps.

OBJECTS AND ADVANTAGES OF THE INVENTION

The objects and advantages of the invention include: to provide a set of tools for use in installing an osteosynthesis apparatus utilizing a set screw with a break-off head; to provide such a set of tools which facilitate manipulation of the components of the osteosynthesis apparatus; to provide such a set of tools which are adapted to grip the head of the set screw; to provide such a set of tools having a handle, a stem and a head with a socket formed therein and having a projection extending into the socket for insertion into a cylindrical bore of a set screw; to provide such a set of tools wherein the projection incorporates an outwardly biasing element for engaging the inner wall of the set screw; to provide such a set of tools wherein the projection is removable from said socket to facilitate cleaning; to provide such a set of tools wherein the projection is formed on the end of a rod insertable through a bore extending through the handle and stem of the tool; to provide such a system incorporating a tool which facilitates the driving of set screws and retrieval of the broken off heads; to provide such a system incorporating a tool which facilitates the driving of a closed end bone screw with a set screw inserted in a set screw bore therein; to provide such a system incorporating a tool which facilitates the installation of caps for open end bone screws, connectors and hooks wherein a set screw is previously inserted in a set screw bore therein; and to provide a tool which facilitates the insertion and manipulation of closed end type bone screws percutaneously.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a set screw having a break-off head for use in an osteosynthesis apparatus.

FIG. 2 is an enlarged front elevational view of the set screw as shown in FIG. 1.

FIG. 3 is a cross-sectional view of the set screw, taken along line 3—3 of FIG. 2.

FIG. 4 is a cross sectional view of the set screw, taken generally along line 4—4 of FIG. 2.

FIG. 5 is a front elevational view on a reduced scale of the set screw showing a lower portion of the set screw engaging a spinal rod secured within a spinal rod bore in a bone screw and showing a head of the set screw broken off.

FIG. 6 is a side elevational view on a reduced scale of a bone screw secured within a vertebra and with portions broken away to show a lower portion of the set screw secured within the bone screw.

FIG. 7 is a fragmentary and exploded front elevational view of a torque wrench of the present invention showing a torque wrench tool body and a set screw engaging insert with one of the set screws secured thereto and with portions of the tool body broken away to show interior detail.

FIG. 8 is an enlarged and fragmentary view of the set screw engaging insert.

FIG. 9 is an enlarged and fragmentary cross-sectional view, taken generally along line 9—9 of FIG. 7, with portions of the set screw removed to show detail thereof.

FIG. 10 is an enlarged and fragmentary bottom plan view of the torque wrench without a set screw secured thereto.

FIG. 11 is a fragmentary front elevational view of the torque wrench with portions broken away to show detail and showing the set screw engaging insert advanced relative to the torque wrench tool body to eject a broken-off head portion of the set screw from a socket of the torque wrench tool body.

FIG. 12 is a fragmentary and exploded front elevational view of a closed end screw driver of the present invention showing a tool body and a set screw engaging insert with a closed end bone screw and with portions of the tool body broken away to show interior detail.

FIG. 13 is an enlarged and fragmentary view of the set screw engaging insert, taken generally along line 13—13 of FIG. 12.

FIG. 14 is an enlarged and fragmentary cross-sectional view, taken generally along line 14—14 of FIG. 12, with portions of a set screw broken away to show detail thereof and showing the closed end screw in phantom lines.

FIG. 15 is a fragmentary front elevational view of a cap inserter of the present invention showing a set screw engaging insert secured within a tool body.

FIG. 16 is a fragmentary side elevational view of the cap inserter, view taken along line 16—16 of FIG. 15.

FIG. 17 is an enlarged and fragmentary bottom plan view of the cap inserter.

FIG. 18 is an enlarged and fragmentary exploded view of the cap inserter having a set screw to be inserted into the set screw engaging insert and wherein the set screw is in turn positioned to be inserted into a saddle cap which is positioned to be inserted into an open ended osteosynthesis connector which is positioned to be secured to an osteosynthesis rod.

FIG. 19 is an enlarged and fragmentary side elevational view of the cap insert and other apparatus shown in FIG. 18, taken generally along line 19—19 of FIG. 18, subsequent to assembly.

FIG. 20 is fragmentary front elevational view of an alternative embodiment of a modified torque wrench of the present invention having a set screw engaging insert secured within a tool body.

FIG. 21 is a bottom plan view of the modified torque wrench.

FIG. 22 is an exploded front elevational view of a threaded bone screw driver of the present invention coupled with a bone screw.

FIG. 23 is an exploded and fragmentary front elevational view of the threaded bone screw driver as shown in FIG. 22 coupled with a cap.

FIG. 24 is an exploded and fragmentary front elevational view of the threaded bone screw driver as shown in FIG. 22 coupled with a hook.

FIG. 25 is a perspective view of a pair of forceps of the present invention with a hook secured thereby.

FIG. 26 is an enlarged and fragmentary view of the forceps shown in FIG. 25 shown in an open position.

FIG. 27 is an enlarged and fragmentary view of the forceps taken generally along line 27—27 of FIG. 25.

FIG. 28 is a view similar to FIG. 5 showing use of an easy out type tool to remove a lower portion of the set screw from a bone screw.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 refers to a set screw for use in osteosynthesis apparatus 2 and, in particular, for use in spinal osteosynthesis apparatus 2. As shown in FIGS. 5 and 6, the set screw 1 is adapted for use in securing an rod 5 in a rod receiving bore 6 of a head or ring 7, from both translational and rotational motion. The ring 7 is of the type formed in the head of a closed end bone screw 10 or the head of a conventional connector or bone hook secured to the bone screw 10. In spinal osteosynthesis, the bone screws 10 are normally referred to as sacral screws or pedicle screws. The rod 5 is of the type including spinal rods for surgical implantation into a patent or may also be the arm or rod portion of a connector or bone hook which collectively are referred to herein as osteosynthesis rods. A threaded set screw receiving bore 11 extends radially through the ring 7 perpendicular to the axis of the rod receiving bore 6.

The set screw 1, as shown in FIGS. 1 through 4, comprises a head 20, of hexagonal external cross-section, and a lower portion 22, having a threaded outer surface 23. The head 20 is relatively elongated to facilitate manipulation of the set screw 1. A point 28 is formed on a lower surface 29 of the set screw 1 centrally thereof so as to extend outwardly along the axis of rotation of the set screw 1. A peripheral notch 32 is formed between the head 20 and the lower threaded portion 22 of the set screw 1 on an outer surface 33 of the set screw 1 the innermost part of the notch 32 forming a circular groove defining a plane that is generally perpendicular to the axis of rotation of the set screw 1.

As best seen in FIG. 3, a cylindrical bore or projection receiving bore 35, comprising an upper bore section 36 and a lower bore section 37 is formed in the set screw 1 and extends through the head 20 and partially through the set screw lower portion 22. The upper bore section 36 generally extends coextensive with the head 20 of the screw 1 and the lower bore section 37 extends partially through the lower portion 22 of the screw 1. The lower bore section 37 preferably has a slightly smaller diameter than the upper bore section 36. A reverse thread 40, of at least one half turn, is formed in an internal wall 41 of the set screw 1 defining the lower bore section 37 near an upper end 42 thereof.

A drive slot 46 extends across a top end 47 of the set screw head 20 having sections that are diagonally spaced on opposite sides of the top end 47. The set screw 1 is preferably driven by a hexagonal socket type wrench as described in more detail below. However, the drive slot 46 is adapted to receive a screw-driver type tool for driving the screw 1 into the set screw receiving bore 11 in some applications.

In use, the set screw 1 may be inserted in the ring 7 after the bone screw 10 is inserted into a bone 50 of a patient and after a rod 5 is inserted through the rod receiving bore 6. To secure the rod 5 in position to prevent further rotational or translational movement of the rod 5 with respect to the rod receiving bore 6, the set screw 1 is further driven through the set screw receiving bore 11 until the point 28 engages and bites into the rod 5. Further driving or tightening of the set screw 1 causes the head 20 of the set screw 1 to shear off at a preselected torque along the narrowest part of the peripheral notch 32, as shown in FIG. 5.

The lower portion 22 of the set screw 1 is preferably sized such that, after the head 20 is sheared off, an upper end 55 of the set screw lower portion 22 is generally flush with an upper edge or upper end 57 of the ring 7 such that no portion, or only a relatively small portion, of the set screw lower portion 22 extends beyond the upper end 57 of the ring 7. Further, after the head 20 is sheared off, the upper end 55 of the set screw lower portion 22 is generally free from burrs or jagged edges.

A set screw torque wrench 60, as shown in FIGS. 7–11, is alternatively used to drive the set screws 1, as noted above, and retrieve the sheared off heads 20 of the screws 1. The torque wrench 60 comprises a tool body 61 having a handle 64, a stem 65 and a head 66 with a socket 67 formed therein. The socket 67 is internally hexagonal in shape and sized and shaped to receive and conform to the head 20 of a set screw 1.

The handle 64 is generally cylindrical and extends perpendicular to the stem 65. An insert receiving bore 69, comprising a first bore portion or handle cavity 70 and a second bore portion or stem bore 71 extends through the tool body 61 and in communication with the socket 67. The handle cavity 70 is formed in the handle 64, perpendicular to a longitudinal axis of the handle 64, and extends substantially through the handle 64 and opening at an upper end 72 thereof. The stem bore 71 is formed in the stem 65 and opens into the handle cavity 70 at one end and the socket 67 at an opposite end. The handle cavity 70 is of larger diameter than the stem bore 71.

A set screw engaging insert 74 comprising a shaft 75 having a cap 76 secured at one end and a nipple or projection 77 extending axially away from an opposite end thereof is sized for insertion into and through the insert receiving bore 69. The shaft 75 is cylindrical. The cap 76 is also cylindrical and of a larger diameter than the shaft 75 and is sized for insertion into the handle cavity 70.

A spring loaded ball detent 80 is secured to or positioned on the cap 76 on a peripheral surface 81 thereof and biasingly engages an inner wall 82 of the handle 64 defining the first bore 70. The spring loaded ball detent 80 functions as securement means for removably securing the cap 76 to the handle 64 and providing resistance to removal of the insert 74 from the tool body 61 that can be overcome by manual pressure. The insert 74 is preferably designed to be removable from the tool body 61 in particular to facilitate cleaning. It is foreseen that other means could be used for removably securing the cap 76 to the handle 64, including other resilient biasing members or structure which provides an interference fit.

A compression type coil spring 85 is positioned in circumscribing relationship with the shaft 75. When the shaft 75 is inserted into the first and second bores 70 and 71, the spring 85 is positioned between a lower surface 86 of the cap 76 and a spring seat or shoulder 87 formed in the handle 64 at the intersection of the handle cavity 70 and the stem bore 71. When the spring 85 is in an uncompressed state, the projection 77 is generally positioned within the socket 67. When the spring 85 is compressed, by manually pushing the cap 76 further into the first bore 70 against the biasing force of the spring 85, the projection 77 is urged to extend out of the socket 67.

The projection 77 is sized for insertion into the cylindrical bore 35 in the set screw 1, when the set screw head 20 is positioned in the socket 67. A peripheral groove 90 extends around the projection 77. A split washer type spring 91 which is compressible is secured to the projection 77 in the peripheral groove 90, such that a portion of the split washer type spring 91 extends beyond a peripheral edge of the projection 77. The outer diameter of the split washer type spring 91 in an uncompressed state is slightly greater than the diameter of the bore 35 in the set screw 1. As the projection 77, which incorporates a frusto-conical tip 92, is inserted into the bore 35 of the set screw 1, a chamfer 94, at an upper end of the set screw 1, facilitates compression of the split washer type spring 91 to permit further insertion of the projection 77 into the bore 35. The compressed split washer type spring 91 biases against an internal wall 95 of the set screw head 20, in order to grip the head 20.

The split washer type spring 91 functions as a resilient biasing member or more generally as retention means for releasably securing the set screw 1 to the projection 77. It is foreseen that a wide variety of resilient biasing members and retention means could be used in association with the projection 77 for securing a set screw 1 thereto including possibly a spring loaded ball detent, a flat spring, a rubber washer or O-ring secured around the projection, coating the projection 77 or the bore 35 in the set screw 1 with a slightly tacky substance, magnetizing the projection 77 or the set screw 1, forming structure on the projection 77 or set screw 1 to create an interference fit or forming the projection 77 of adjacent biasable strips or segments such that the entire projection is biasable.

Drive flanges, ears, projections or tabs 96 extend radially outward from the projection 77 at an upper end thereof and on opposite sides of the projection 77. The tabs 96 are sized for insertion into the drive slot 46 extending across the top end 47 of a set screw 1.

The torque wrench 60 is used to tighten a set screw 1 until a preselected torque is applied to the set screw 1 at which time the head 20 breaks off. After the head 20 breaks off, the head 20 is held by the projection 77 and may be removed from an operating cavity (not shown) in a patient by simply withdrawing the wrench 60. After the torque wrench head 66 is removed from the operating cavity, the cap 65 may be pressed further into the first bore 70 against the biasing force of the spring 85 to advance the projection 77, with the set screw head 20 secured thereto, so as to extend out of the socket 67, to permit easy manual removal of the set screw head 20 from the projection 77.

The set screw 1 may also be pre-loaded into the bone screw 10, or related structure, prior to insertion into the patient. For example, the set screw 1 may be manually partially inserted in the set screw receiving bore 11 of a bone screw 20 or a connector before insertion in a patient and rotated a sufficient number of turns such that the set screw 1 is secured in the set screw receiving bore 11, but does not extend extensively into the rod receiving bore 6. The bone screw 10, with the set screw 1 secured thereto, may then be driven into the appropriate bone 50 of a patient. After a rod 5 is inserted through the rod receiving bore 6 of the bone screw 10, the set screw 1 is tightened, as discussed above.

A closed end screw driver 101, as shown in FIGS. 12–14 is also used to drive a closed end bone screw 10 and is particularly adapted for driving a closed end bone screw 10 having a set screw 1 pre-loaded into the set screw receiving bore 11. The closed end screw driver 101 comprises a tool body 102 having a handle 105, a stem 106, and a head 107 having a socket 108 formed therein.

An insert receiving bore 113, comprising a first bore portion or handle cavity 114 and a second bore portion or stem bore 115 extends through the tool body 102 and in communication with the socket 108. The handle cavity 114 is formed in the handle 105 along a central axis thereof and extends substantially through the handle 105 and opens at an upper end 116 thereof. The stem bore 115 is formed in the stem 106 and opens into the handle cavity 114 at one end and the socket 108 at an opposite end. The handle cavity 114 is of larger diameter than the stem bore 115.

The handle 105 is preferably cylindrical. An outer surface 118 of the handle 105 is knurled to facilitate gripping. The stem 106 extends in axial alignment with the handle 105 from a lower end 119 thereof.

A pair of depending abutment flanges 125 depend from the head 107 of the closed end screw driver 101 on opposite sides thereof. The flanges, projections, tabs or ears 125 are sized, shaped and spaced apart to fit over the end of the head or ring 7 of the closed end bone screw 10 and to abut against opposed faces 127 thereof so as to receive a portion of the ring 7 therebetween. A semicircular notch 129 is formed along a lower edge of each of the ears 125 to prevent the ears 125 from obstructing access to the rod receiving bore 6 in the bone screw head or ring 7.

The socket 108 of the closed end screw driver 101 is generally interiorly cylindrical in shape and slightly larger in diameter than the diameter of the set screw head 20 such that the head 20 of a set screw 1 may be freely rotated within the socket 108.

A set screw engaging insert 134 comprising a shaft 135 having a cap 136 secured at one end and a nipple or projection 137 extending axially away from an opposite end thereof is sized for insertion into and through the insert receiving bore 113 in the tool body 102. The shaft 135 is cylindrical. The cap 136 comprises an upper cap portion 138 and a lower cap portion 139. The upper cap portion 138 is cylindrical and of the same diameter as the outer surface 118 of the handle 105. The lower cap portion 139 is cylindrical and has a diameter slightly smaller than the diameter of the handle cavity 114 and is insertable into the handle cavity 114 from the upper end 116 thereof such that the upper cap portion 138 extends in axial alignment beyond the upper end 116 of the handle 105. An outer surface 140 of the upper cap portion 138 is also knurled to facilitate gripping.

Spring loaded ball detents 142 are secured to or positioned on the lower cap portion 139 on a peripheral surface 143 thereof and biasingly engage an inner wall 144 of the handle 105 defining the handle cavity 114. Engagement of the inner wall 144 of the handle 105 by the spring ball detents 142, resists removal of the shaft 135 from the handle cavity 114 and the stem bore 115, but permits the cap 136 to be rotated relative to the handle 105 and allows removal by application of manual pressure.

The spring loaded ball detents 142 function as securement means for removably securing the cap 136 to the handle 105 and providing resistance to removal of the insert 134 from the tool body 102. The insert 134 is preferably designed to be removable from the tool body 102 in particular to facilitate cleaning. It is foreseen that other means could be used for removably securing the cap 136 to the handle 105 including other resilient biasing members or structure which provides an interference fit.

The projection 137 on the shaft 135 of the set screw engaging insert 134 for the closed end screw driver 101 is identical to the projection 77 on the end of the shaft 75 of the set screw engaging insert 74 for the torque wrench 60 and includes a split washer type spring 150 secured in a peripheral notch 151 on the projection which has a frusto-conical tip 152. Drive ears 155 extend radially outward from the projection 137 at an upper end thereof and on opposite sides of the projection 137. The ears 155 are sized for insertion into the drive slot 46 extending across the top end 47 of the set screw 1.

With the set screw engaging insert 134 inserted within the tool body 102 such that the projection 137 extends into the socket 108, the socket head 107 of the closed end screw driver 101 may be positioned over and into engaging relationship with the head or ring 7 of a closed end bone screw 10 having a set screw 1 pre-loaded thereon, such that the set screw 1 extends into the socket 108 and the projection 137 extends into the bore 35 of the set screw 1, as is shown in FIG. 14 with the closed end set screw 10 shown in phantom lines for clarity. Biasing engagement of the split washer type spring 150 against an internal wall 95 of the set screw 1 grips or holds the set screw 1 onto the projection 137 and therefor grips or holds the closed end bone screw 10, to which the set screw 1 is attached, to the closed end screw driver 101.

The split washer type spring 150 functions as a resilient biasing member or more generally as retention means for releasably securing the set screw 1 to the projection 137. It is foreseen that a wide variety of resilient biasing members and retention means could be used in association with the projection 137 for securing a set screw 1 thereto including possibly a spring loaded ball detent, a flat spring, a rubber washer or O-ring secured around the projection, coating the projection 137 or the bore 35 in the set screw 1 with a slightly tacky substance, magnetizing the projection 137 or the set screw 1, forming structure on the projection 137 or set screw 1 to create an interference fit or forming the projection 137 of adjacent biasable strips or segments such that the entire projection is biasable.

With the closed end bone screw 10 secured to the closed end screw driver 101, as discussed, the driver 101 can then be used to drive the closed end bone screw 10 into the selected bone 50 by rotating and pushing downward on the handle 105. After the closed end bone screw 10 is driven into the bone, a rod 5 can be inserted through the rod receiving bore 6 with the closed end screw driver 101 still secured to the closed end bone screw 10.

The set screw engaging insert 134 can then be used to partially tighten down the set screw 1 by rotating and pushing down on the upper cap portion 138 relative to the handle 105. The shaft 135 is preferably sized such that when the closed end bone screw 10 is secured to the closed end screw driver 101, a lower edge or shoulder 160 of the upper cap portion 138 is spaced slightly above the upper end 116 of the handle 105. Such spacing being sufficient to compensate for the distance the set screw engaging insert 134 must be driven downward relative to the handle 105 to drive the set screw 1 into engaging relationship with a rod 5 in the rod receiving bore 6 of the bone screw 10.

The drive ears 155 are generally not strong enough to provide the torque necessary to shear off the set screw head 20. The torque wrench 60 is preferably used for such purposes. However, if the drive ears 155 are successfully used to provide the required torque to shear off the set screw head 20, then the shaft 135 and the projection 137 with the head 20 secured thereto can be retracted through the insert receiving bore 113 of the tool body 102 to permit removal of the head 20 from the projection 137.

In addition to closed end type bone screws, connectors and hooks, open end type bone screws, connectors and hooks are used with the described tools and the osteosynthesis apparatus 2.

FIGS. 15–19 show a cap inserter or saddle cap inserter 170 which is adapted for use in inserting a cap, saddle or saddle cap 172 into an open end type implant 173, which, as shown in FIG. 18, comprises a connector or osteosynthesis. The connector 173 comprises a head or body 175 and a connector rod 176 extending away from the body 175. An upwardly opening U-shaped channel or groove 177 is formed in the connector body 175 between opposed channel sidewalls 178 and 179. A curved slot 180 and 181 is formed in each sidewall 178 and 179 respectively on inner opposed faces thereof.

The saddle cap 172 includes a central portion 188 and outwardly extending curved flanges or tongues 189 and 190 formed on opposite sides thereof. A downwardly opening rod conforming channel 191 is formed on the bottom of the cap central portion 188. A set screw receiving bore 192 extends through the central portion 188 from an upper end 193 thereof to the rod conforming channel 191.

The saddle cap 172 includes a front face 194 and a rear face 195. Leading edges 196 of the tongues 189 and 190 adjacent the cap front face 194 are slightly curved.

After a rod 5 is inserted into the U-shaped channel 177 of the connector 173 by dropping it therein, a saddle cap 172 may be attached to the connector 173 to secure the rod 5 therein. A set screw 1 that is positioned in the set screw receiving bore 192 in the cap 172 is then tightened to fix the relative position of the rod 5 relative to the connector 173. The set screw 1 is tightened until a preselected torque is exceeded and the head 20 breaks off.

The saddle cap 172 is attached to the body 175 of a connector 173 by positioning the saddle cap 172 adjacent a connector 173 at a slightly downward angle such that the leading edges 196 of the tongues 189 and 190 are aligned with one end of the curved slots 180 and 181 in the connector 173. The saddle cap 172 is then advanced forward and rotated slightly upward such that the tongues 189 and 190 extend into the curved slots 180 and 181 respectively.

The saddle cap 172 is preferably wedge shaped in that the distance across the rear face 195 of the saddle cap 172 is slightly greater than the distance across the front face 194 of the saddle cap 172 and the distance between the sidewalls 178 and 179 along the slots 180 and 181. During insertion of the saddle cap 172 to the connector body 175, the wedge shape of the saddle cap 172 can be rotated sufficiently to wedge against the sidewalls 178 and 179 to form an interference fit between the saddle cap 172 and the sidewalls 178 and 179. In this configuration the saddle cap 172 is slightly tilted relative to the rod 5 so that both the front lower edge of the cap 172 and the set screw 1 bite into the rod 5 in opposite directions thereby further locking the rod 5 in the connector 173.

The cap inserter 170 comprises a tool body 202 having a handle 205, a stem 206, and a head 207 having a socket 208 formed therein. An insert receiving bore 213, comprising a first bore portion or handle cavity 214 and a second bore portion or stem bore 215 extends through the tool body 202 and in communication with the socket 208. The handle cavity 214 is formed in the handle 205 along a central axis thereof and extends substantially through the handle 205 and opens at an upper end 216 thereof. The stem bore 215 is formed in the stem 206 and opens into the handle cavity 214 at one end and the socket 208 at an opposite end. The handle cavity 214 is of larger diameter than the stem bore 215.

The handle 205 is preferably cylindrical. An outer surface 218 of the handle 205 is knurled to facilitate gripping. The stem 206 extends in axial alignment with the handle 205 from a lower end 219 thereof.

A tab or abutment member 225 depends from a lower end 226 of the head 207 of the cap inserter 170 on one side thereof. The abutment member 225 is adapted for positioning in abutting relationship against the rear face 195 of a saddle cap 172. A semicircular notch 229 is formed along a lower edge of the abutment member 225 corresponding to the periphery of the rod conforming channel 191 in the saddle cap 172 to provide clearance for the rod 5 positioned in the U-shaped channel 177.

The socket 208 of the saddle cap inserter 170 is generally cylindrical and slightly larger in diameter than the diameter of the set screw head 20 such that the head 20 of a set screw 1 may be freely rotated within the socket 208.

The set screw engaging insert 134 is adapted for interchangeable use with the closed end screw driver 101 and the saddle cap inserter 170. The shaft 135 of the insert 134 is sized for insertion into and through the insert receiving bore 213 of the tool body 202. The diameter of the outer surface 218 of the handle 205 is the same as the diameter of the upper cap portion 138. The diameter of the handle cavity 214 is slightly greater than the diameter of the lower cap portion 139 and the lower cap portion 139 is insertable into the handle cavity 214 from the upper end 216 thereof such that the upper cap portion 138 extends in axial alignment beyond the upper end 216 of the handle 205.

The spring loaded ball detents 142 on the lower cap portion 139 biasingly engage an inner wall 244 of the handle 205 defining the handle cavity 214. Engagement of the inner wall 244 of the handle 205 by the spring loaded ball detents 142, resists removal of the insert 134 from the handle cavity 214 and the second bore 216, but permits the insert 134 to be rotated relative to the tool body 202.

The saddle cap inserter 170 is particularly adapted for use in inserting saddle caps 172 having set screws 1 preloaded in the set screw receiving bores 192 of the saddle caps 172. With the set screw engaging insert 134 inserted into the handle 205 and stem 206, such that the projection 137 extends into the socket 208, the head 20 of a set screw 1 secured to a cap 172 can be inserted into the socket 208 such that the projection 137 extends into the bore 35 in the set screw 1 and such that the abutment member 225 extends in abutting relationship with the rear face 195 of the saddle cap 172. The split washer type spring 150 biasingly engages an internal wall 95 of the set screw 1 and thereby grips or holds the set screw 1 onto the projection 137 and in turn grips or holds the saddle cap 172, to which the set screw 1 is attached, to the cap inserter 170. Abutment of the abutment member 225 against the rear face 195 of the saddle cap 172 prevents the saddle cap 172 from rotating relative to the set screw 1 during manipulation and insertion of the saddle cap 172 and thereby facilitates insertion.

With the saddle cap 172 secured to the saddle cap inserter 170, the saddle cap inserter 170 can then be used to insert the saddle cap 172 into the open end type implant or connector 173 as previously discussed. After the saddle cap 172 is inserted, with a rod 5 in place between the saddle cap 172 and the connector body 175, the set screw engaging insert 134 can then be used to partially tighten the set screw 1 by rotating and pushing down on the upper cap portion 138 relative to the handle 205. The shaft 135 is preferably sized such that when a saddle cap 172 is secured to the saddle cap inserter 170, a lower edge or shoulder 160 of the upper cap portion 138 is spaced slightly above the upper end 216 of the handle 205. Such spacing being sufficient to compensate for the distance the set screw engaging insert 134 must be driven downward relative to the handle 205 to drive the set screw 1 into engaging relationship with a rod 5 secured between the saddle cap 172 and the connector body 175.

FIGS. 20 and 21 show a torque wrench 251 which is an alternative embodiment of the torque wrench 60. The torque wrench 251 comprises a tool body 252 having a handle 255, a stem 256, and a socket head 257 having a socket 258 formed therein. An insert receiving bore 263, comprising a first bore portion or handle cavity 264 and a second bore portion or stem bore 265 extends through the tool body 252 and in communication with the socket 258. The handle cavity 264 is formed in the handle 255 along a central axis thereof and extends substantially through the handle 255 and opens at an upper end 266 thereof. The stem bore 265 is formed in the stem 256 and opens into the handle cavity 264 at one end and the socket 258 at an opposite end. The handle cavity 264 is of larger diameter than the stem bore 265.

The handle 255 is preferably cylindrical. An outer surface 268 of the handle 255 is knurled to facilitate gripping. The stem 256 extends in axial alignment with the handle 255 from a lower end 269 thereof. The socket 258 of the torque wrench 251 is internally hexagonal and sized and shaped to conform to the shape of a set screw head 20.

The set screw engaging insert 134 is adapted for interchangeable use with the closed end screw driver 101, the saddle cap inserter 170 and the torque wrench 251. The shaft 135 of the insert 134 is sized for insertion into and through the insert receiving bore 263 of the tool body 252. The diameter of the outer surface 268 of the handle 255 is the same as the diameter of the upper cap portion 138. The diameter of the handle cavity 264 is slightly greater than the diameter of the lower cap portion 139 and the lower cap portion 239 is insertable into the handle cavity 264 from the upper end 266 thereof such that the upper cap portion 138 extends in axial alignment beyond the upper end 266 of the handle 255.

The spring loaded ball detents 142 on the lower cap portion 139 biasingly engage an inner wall 284 of the handle 255 defining the handle cavity 264. Engagement of the inner wall 284 of the handle 255 by the spring loaded ball detents 142, resists slippage of the insert 134 from the insert receiving bore 263, but allows manual removal.

The torque wrench 251 can be used like the torque wrench 60 to tighten down a set screw 1 and retain and retrieve the broken off set screw head 20. With the set screw engaging insert 134 secured to the tool body 252 such that the projection 137 extends into the socket 258, a set screw 1 can be inserted into the socket 258 such that the projection 137 extends into the bore 35 in the set screw 1. The washer type spring 150 biasingly grips or holds the set screw 1 to the projection 137 to facilitate manipulation of the torque wrench 251 with the set screw 1 releasably secured therein.

Another tool of the present invention, as shown in FIG. 22, is hereinafter referred to as a threaded implant installer 290. The threaded implant installer 290 comprises a stem 291 having a handle 292 secured at one end and a threaded tip 293 at an opposite end. The threaded tip 293 is sized for insertion into and threaded coupling within the set screw receiving bore 11 in the bone screw 10 (FIG. 22), the set screw receiving bore 192 in a cap 172 (FIG. 23), a set screw receiving bore 295 in a hook 296 (FIG. 24) or a set screw receiving bore in other pieces of osteosynthesis hardware. The threaded implant installer 290 is particularly useful in minimally invasive or percutaneous type surgery wherein the bone screw 10, saddle cap 172, hook 296 or related item is inserted into the body through a relatively small incision. The threaded coupling between the threaded bone screw driver 290 and the bone screw 10 or related hardware prevents the bone screw 10 or related item from being pulled from the driver 290, if the bone screw 10 or related hardware must be retracted through the incision.

After a closed end type bone screw 10 has been driven into a bone 50 with driver 290, and a rod 5 has been inserted in the rod receiving bore 6 therein, the torque wrench 60, with a set screw 1 secured on the projection 77, can be used to insert the set screw 1 into the set screw receiving bore 11 of the bone screw 10 and to then tighten the set screw 1, break off the head 20 and remove the broken off head 20. Similar steps can be utilized to install a set screw 1 in the set screw receiving bore of related implants or hardware such as saddle cap 172 or hook 296.

A pair of forceps 300, as shown in FIGS. 25–27, is adapted for use in gripping and manipulating implants, such as hooks 296, bone screws 10, and caps 172, with one of the set screws 1 secured within the set screw receiving bore 11, 192 and 295 respectively. The forceps 300 comprises a first arm 301 and a second arm 302 pivotally secured together in a scissor like fashion. Each arm 301 and 302 comprises a handle portion 311 and 312 respectively and a grasping portion 313 and 314 respectively. The grasping portions 313 and 314 are adapted to cooperatively engage and grasp an implant such as one of the hooks 296 with a set screw 1 secured thereto as shown in FIGS. 25–27.

In particular, the grasping portions 313 and 314 are adapted for grasping a hook 296 (or other implant) with a set screw 1 secured within the set screw receiving bore 295 such that the point 28 of the set screw 1 does not extend into a rod receiving bore 316 extending through the hook 296 transverse to and in communication with the set screw receiving bore 295. With the set screw 1 so positioned in the set screw receiving bore 295 of the hook 296, a gap 317 is formed between a lower end 318 of the set screw head 20 and a set screw receiving end or distal end 319 of the hook 296. The peripheral notch 32 and a portion of the threaded outer surface 23 are generally exposed by the gap 317.

First and second socket halves 321 and 322 are formed in the ends of the grasping portions 313 and 314 respectively such that when the first and second grasping portions 313 and 314 are pivotally advanced together the first and second socket halves 321 and 322 form a socket 323. A ridge or wall 325 extends across the first socket half 321 dividing the first socket half 321 into an inner socket portion 326 and an outer socket portion 327 which correspond with an inner socket portion 328 and an outer socket portion 329 of the second socket half 322.

The first socket half 321 is sized such that one of the hooks 296 with a set screw 1 secured thereto as discussed above, may be positioned relative to the first grasping portion 313 such that the set screw head 20 is positioned in the inner socket portion 326, the distal end 319 of the hook 296 is positioned within the outer socket portion 327 and the ridge 325 extends into the gap 317. The gap 317 extends adjacent to the lower end 318 of the set screw head 20.

The second grasping portion 314 is then advanced toward the first grasping portion 313 until the second grasping portion 314 engages the hook 296 with the set screw 1 secured thereto. The first and second grasping portions 313 and 314 are releasably locked in place by a conventional clamping assembly such as first and second saw toothed clamping members 341 and 342 on the first and second handle portions 311 and 312 respectively.

With the first and second grasping portions 313 and 314 locked in engaging relationship with the distal end 319 of the hook 296 and the set screw 1, a user can securely grasp the hook 296 for manipulation relative to a patient. Engagement of the lower end 318 of the set screw head 20 by the ridge 325 prevents the hook 296 with the set screw 1 attached thereto from being pulled out of the grasp of the first and second grasping portions 313 and 314 during manipulation.

It is foreseen that a ridge similar to ridge 325 could be formed in the second grasping portion 314 and extend across the second socket half 322 between the inner and outer socket portions 328 and 329 thereof. However, use of two such ridges is more likely to damage the threads on the set screw threaded outer surface 23 and therefore it is preferable to utilize only one such ridge 325.

First and second semicircular notches 346 and 347 are formed in distal ends of the first and second grasping portions 313 and 314 of the forceps 300. The notches 346 and 347 prevent the distal ends of the grasping portions 313 and 314 from obstructing access to the rod receiving bore 316 of the hook 296 when the hook is secured between the grasping portions 313 and 314.

The forceps 300 are preferably adapted for use in grasping and manipulating other implants including bone screws 11, saddle caps 172 or closed end connectors (not shown).

After the head 20 has been sheared off from the set screw lower portion 22, the lower bore section 37 is adapted to receive an easy out type tool 299 to permit removal of the set screw lower portion 22, when necessary, as is shown in FIG. 23. The reverse thread 40 allows the easy out type tool 299 to begin to grip the sidewall 37 and thus facilitates gripping of a substantial portion of the sidewall 37 by the tool 299 to purchase enough leverage to allow removal of the screw lower portion 22 from the bone screw 10.

It is foreseen that the projections 77 or 137 could be integrally formed with an associated tool body and extend from an internal end of the socket, axially into the socket and toward an open end of the socket. It is also foreseen that the tools of the present invention could be adapted for use with set screws having a projection receiving bore of various cross-sections including hexagonal, rectangular, ovate or a torx type bore in which case the associated projection of the tools would be configured to correspond or cooperate with the shape of the projection receiving bore. Further it is foreseen that although the tool bodies, the insert receiving bores and the set screw engaging inserts are generally shown as having circular cross-sections the cross-sections of some or all of these items could be of various configurations including rectangular, hexagonal, ovate or other configurations.

It is to be understood that while certain forms of the present invention have been illustrated and described herein, it is not to be limited to the specific forms or arrangement of parts described and shown.

What is claimed and desired to be secured by Letters Patent is as follows:

1. A tool for use in installing an osteosynthesis apparatus utilizing a set screw having a head with an axially extending bore formed therein; said tool comprising:
    a) a handle;
    b) a stem connected at one end to said handle;
    c) a socket head connected to said stem at an end opposite said handle and having a socket formed therein; said socket sized to receive at least a portion of said set screw head;
    d) a projection extending axially into said socket and sized for snug insertion into at least a portion of the set screw bore;
    e) a resilient biasing member secured to said projection for biasingly engaging an inner surface of the set screw head; and wherein
    f) said resilient biasing member comprises a split washer type spring secured around said projection in a circumferential notch formed on an outer surface of said projection.

2. A tool for use in installing an osteosynthesis apparatus utilizing a set screw having a head and an axially extending bore formed therein; said tool comprising:
    a) a handle having a cavity formed therein opening at an upper end thereof;
    b) a stem connected at one end to said handle and having a bore extending therethrough; said stem bore opening into said handle cavity;
    c) a socket head connected to said stem at an end of said stem opposite said handle and having a socket formed therein in communication with said stem bore; said socket sized and shaped to receive at least a portion of the set screw head;
    d) a set screw engaging insert comprising a shaft having a screw engaging projection extending from one end thereof; said shaft sized for insertion through said handle cavity and said stem bore such that said set screw engaging projection extends axially into said socket; said screw engaging projection being sized for insertion into at least a portion of the set screw bore;
    e) a resilient biasing member secured to said projection for biasingly engaging an inner surface of the set screw head; and
    f) said resilient biasing member comprises a split washer type spring secured around said projection in a circumferential notch formed on an outer surface of said projection.

3. A tool for use in installing an osteosynthesis apparatus utilizing a set screw having a head and an axially extending bore formed therein; said tool comprising:
    a) a handle having a cavity formed therein opening at an upper end thereof;
    b) a stem connected at one end to said handle and having a bore extending therethrough; said stem bore opening into said handle cavity;
    c) a socket head connected to said stem at an end of said stem opposite said handle and having a socket formed therein in communication with said stem bore; said socket sized and shaped to receive at least a portion of the set screw head;
    d) a set screw engaging insert comprising a shaft having a screw engaging projection extending from one end thereof; said shaft sized for insertion through said handle cavity and said stem bore such that said set screw engaging projection extends axially into said socket; said screw engaging projection being sized for insertion into at least a portion of the set screw bore;
    e) a pair of abutment ears depending from a lower end of said socket head on opposite sides thereof;
    f) said set screw engaging insert includes a cap secured to said shaft on an end opposite said projection; said cap includes securement means for removably securing said cap to said handle such that said set screw engaging insert is rotatable relative to said handle, said stem and said socket head; and
    g) said securement means comprise a spring loaded ball detent positioned on an outer surface of said cap.

4. A set of tools for use in installing an osteosynthesis apparatus utilizing a set screw having a head and an axially extending bore formed in the head; said set of tools comprising:

17 a) a plurality of tool bodies each comprising:
  1) a handle having a cavity formed therein opening at an upper end thereof;
  2) a stem connected at one end to said handle and having a bore extending therethrough; said stem bore opening into said handle cavity; and
  3) a socket head connected to said stem at an end of said stem opposite said handle and having a socket formed therein in communication with said stem bore; said socket sized and shaped to receive at least a portion of the set screw head; and
b) a set screw engaging insert comprising a shaft having a screw engaging projection extending from one end thereof; said shaft sized for interchangeable insertion through said handle cavity and said stem bore of said tool bodies such that said screw engaging projection extends axially into said socket of said respective tool body; said screw engaging projection is sized and shaped for insertion into at least a portion of the set screw bore;
c) a resilient biasing member secured to said projection for biasingly engaging the inner surface of the set screw head;
d) said resilient biasing member further includes a split washer type spring secured around said projection in a circumferential notch formed on an outer surface of said projection.

5. A set of tools for use in installing an osteosynthesis apparatus utilizing a set screw having a head and an axially extending bore formed in the head; said set of tools comprising:
a) a plurality of tool bodies each comprising:
  1) a handle having a cavity formed therein opening at an upper end thereof;
  2) a stem connected at one end to said handle and having a bore extending therethrough; said stem bore opening into said handle cavity; and
  3) a socket head connected to said stem at an end of said stem opposite said handle and having a socket formed therein in communication with said stem bore; said socket sized and shaped to receive at least a portion of the set screw head; and
b) a set screw engaging insert comprising a shaft having a screw engaging projection extending from one end thereof; said shaft sized for interchangeable insertion through said handle cavity and said stem bore of said tool bodies such that said screw engaging projection extends axially into said socket of said respective tool body; said screw engaging projection is sized and shaped for insertion into at least a portion of the set screw bore;
c) said set screw engaging insert includes a cap secured to said shaft on an end opposite said projection; said cap includes securement means for selectively and removably securing said cap to said handles such that said set screw engaging insert is rotatable relative to said handle, said stem and said socket head of said respective tool body; and
d) said securement means comprises a spring loaded ball detent positioned on an outer surface of said cap.

6. A tool for use in installing an osteosynthesis apparatus utilizing a set screw having a head and an axially extending bore formed therein; said tool comprising:
a. a handle having a cavity formed therein opening at an upper end thereof;

18 b. a stem connected at one end to said handle and having a bore extending therethrough; said stem bore opening into said handle cavity;
c. a socket head connected to said stem at an end of said stem opposite said handle and having a socket formed therein in communication with said stem bore; said socket sized and shaped to receive at least a portion of the set screw head;
d. a tab depending from a lower end of said socket head; and
e. a set screw engaging insert comprising a shaft having a screw engaging projection extending from one end thereof; said shaft sized for insertion through said handle cavity and said stem bore such that said set screw engaging projection extends axially into said socket; said screw engaging projection being sized for insertion into at least a portion of the set screw bore; said set screw engaging insert further includes a cap secured to said shaft on an end opposite said projection; said cap includes a spring loaded ball detent positioned on an outer surface of said cap for removably securing said cap to said handle such that said set screw engaging insert is rotatable relative to said handle, said stem and said socket head.

7. The tool as in claim 6 further including:
a. retention means on said projection for releasably securing the set screw to said projection.

8. The tool as in claim 6 further including:
a. a resilient biasing member secured to said projection for biasingly engaging an inner surface of the set screw head.

9. The tool as disclosed in claim 6 wherein:
a. a pair of drive ears extend outward from said set screw engaging projection on opposite sides thereof and are sized and shaped for insertion in a drive slot on an upper end of the set screw.

10. The tool as disclosed in claim 6 wherein:
a. said socket is shaped to conform to the shape of an outer surface of the set screw head.

11. The tool as disclosed in claim 10 further comprising:
a. means for removably securing said set screw engaging insert within said handle cavity and said stem bore such that when said set screw engaging insert is secured therein said projection is advanceable between a retracted position wherein a substantial portion of said projection is positioned in said socket and an extended position wherein a substantial portion of said projection is advanced out of said socket.

12. The tool as disclosed in claim 10 including:
a. an insert cap secured to said shaft of said set screw engaging insert on an end opposite said projection;
b. a spring seat formed in said handle adjacent the intersection of said handle cavity with said stem bore; and
c. a compression type coil spring positioned on said shaft below said cap such that when said shaft is inserted through said handle cavity and said stem bore said spring is positioned between said spring seat and said cap.

13. The tool as in claim 10 further including:
a. a resilient biasing member secured to said projection for biasingly engaging the inner surface of the set screw head.

14. The tool as disclosed in claim 6 adapted for use in manipulating an implant having one of the set screws threadingly secured within a set screw receiving bore therein; said tool further comprising:

a. a pair of abutment ears depending from a lower end of said socket head on opposite sides thereof.

15. The tool as in claim 14 further including:

a. a resilient biasing member secured to said projection for biasingly engaging the inner surface of the set screw head.

16. The tool as in claim 14 wherein:

a. said set screw engaging insert includes a cap secured to said shaft on an end opposite said projection; said cap includes securement means for removably securing said cap to said handle such that said set screw engaging insert is rotatable relative to said handle, said stem and said socket head.

\* \* \* \* \*